US00PP32738P2

(12) United States Plant Patent
Prukngen

(10) Patent No.: US PP32,738 P2
(45) Date of Patent: Jan. 5, 2021

(54) ***CANNA* PLANT NAMED 'WHITE TIGER'**

(50) Latin Name: ***Canna* x *generalis***
Varietal Denomination: White Tiger

(71) Applicant: Brian's Botanicals, Louisville, KY (US)

(72) Inventor: Somchai Prukngen, Bangkok (TH)

(73) Assignee: BRIAN'S BOTANICALS, Louisville, KY (US)

( * ) Notice: Subject to any disclaimer, the term of this patent is extended or adjusted under 35 U.S.C. 154(b) by 0 days.

(21) Appl. No.: 16/873,514

(22) Filed: Apr. 24, 2020

(51) Int. Cl.
*A01H 5/02* (2018.01)

(52) U.S. Cl.
USPC ..... Plt./415

(58) Field of Classification Search
USPC ..... Plt./415
CPC ..... A01H 6/00; A01H 5/02
See application file for complete search history.

*Primary Examiner* — Keith O. Robinson
(74) *Attorney, Agent, or Firm* — Penny J. Aguirre

(57) ABSTRACT

A new cultivar of *Canna* plant named 'White Tiger' that is characterized by its compact and mid-sized plant habit, its flowers that are white in color, its heavily striated (variegated) foliage with alternating striations of green and yellow. and its flowers that are medium to large in size.

2 Drawing Sheets

Botanical classification: *Canna* x *generalis*.
Cultivar designation: 'White Tiger'.

BACKGROUND OF THE INVENTION

The present invention relates to a new and distinct cultivar of *Canna* x *generalis* known as 'White Tiger' and is hereinafter referred to as 'White Tiger'. 'White Tiger' is a new cultivar of *Canna* lily, which is grown as an annual or perennial depending on climate zone and for use in containers and in the landscape.

The new cultivar arose from an ongoing breeding program by the Inventor in Bangkok, Thailand with the goal of developing new cultivars of *Canna* with unique flower colors combined with yellow striated foliage.

The new cultivar was derived from a cross made by the Inventor in June of 2015 between unnamed and unpatented proprietary plants of *Canna* x *generalis* from the Inventor's breeding program as both the female and male parents. 'White Tiger' was selected as a single unique plant from amongst the seedling that arose from the above cross in October of 2016.

Asexual propagation of the new cultivar was first accomplished by rhizome division by the Inventor in Bangkok, Thailand in June of 2017. Asexual propagation of the new cultivar by rhizome division has shown that the unique characteristics of 'White Tiger' are stable and reproduced true to type in successive generations.

SUMMARY OF THE INVENTION

The following traits have been repeatedly observed and represent the characteristics of the new cultivar. These attributes in combination distinguish 'White Tiger' as a new and unique cultivar of *Canna*.

1. 'White Tiger' exhibits a compact and mid-sized plant habit.
2. 'White Tiger' exhibits flowers that are white in color.
3. 'White Tiger' exhibits heavily striated (variegated) foliage with alternating striations of green and yellow.

4. 'White Tiger' exhibits flowers that are medium to large in size.

The female plant of 'White Tiger' differs from 'White Tiger' in having flowers that are yellow in color, less striated foliage and a more compact plant habit. The male plant of 'White Tiger' differs from 'White Tiger' in having green foliage that has no striation and a larger plant habit. 'White Tiger' can be most closely compared to the cultivars 'Bengal Tiger' and 'Minerva' (both unpatented). Both are similar to 'White Tiger' in having yellow and green striated foliage. 'Bengal Tiger' differs from 'White Tiger' in having a much taller plant height and flowers that are orange in color. 'Minerva' differs from 'White Tiger' in having flowers that are yellow in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Brian's Botanicals and Plant Delights Nursery.

BRIEF DESCRIPTION OF THE DRAWINGS

The accompanying colored photographs illustrate the overall appearance and distinct characteristics of the new *Canna*. The photographs were taken of 1-year-old plants as grown under 6 mm poly and natural lighting in 2-gallon containers in Louisville, Ky.

Figure 1:
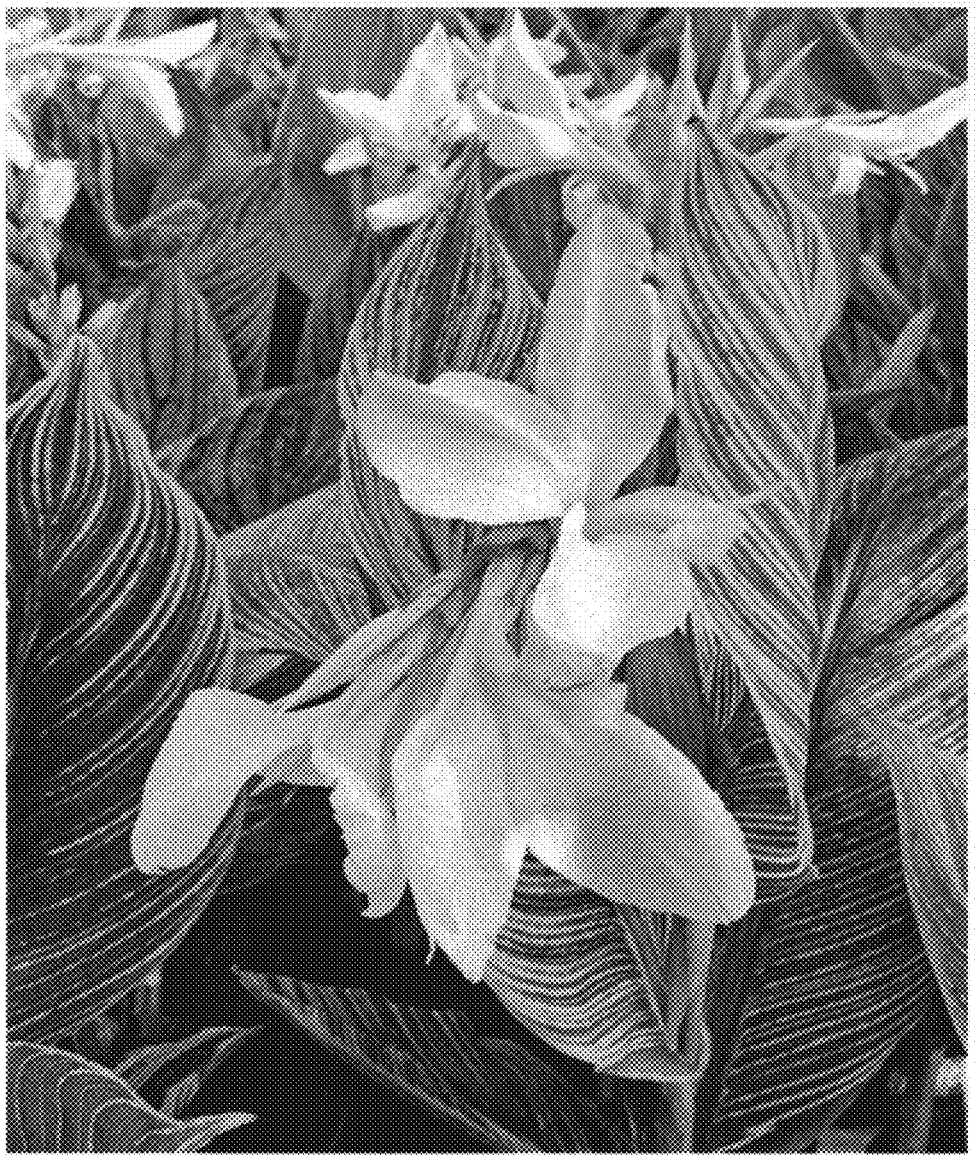
FIG. 1 provides a side view of a plant of 'White Tiger' in bloom.
Figure 2:
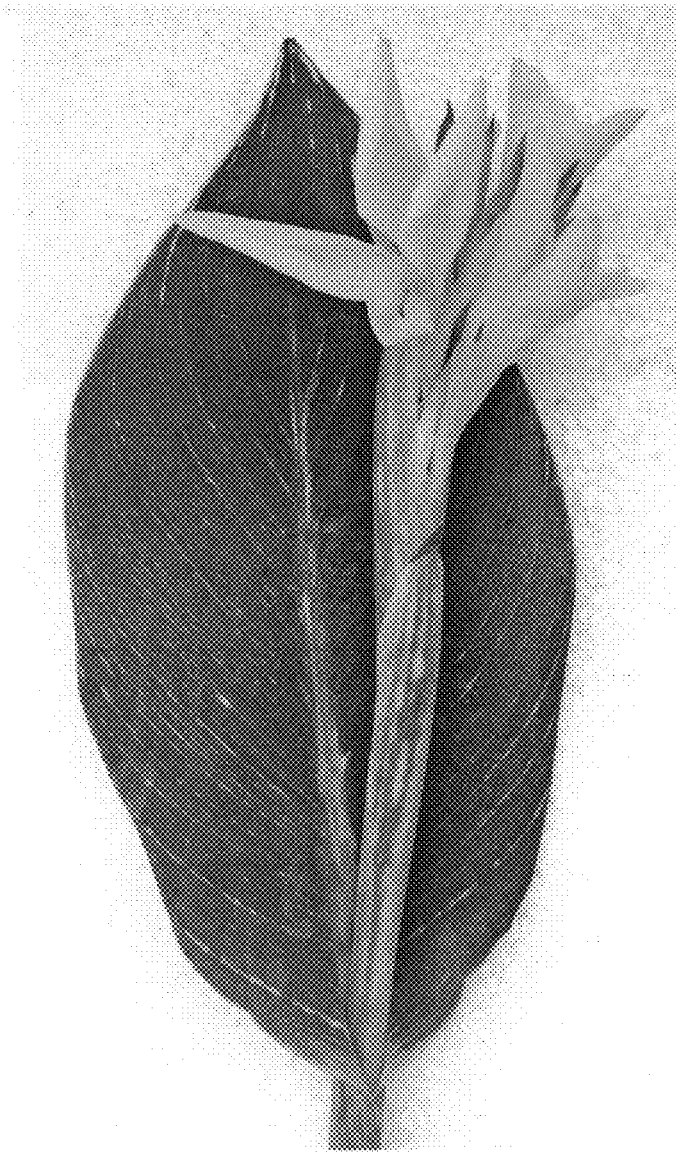

The photograph in FIG. 2 provides a close-up top view of an inflorescence and a leaf of 'White Tiger'.

The colors in the photographs are as close as possible with the photographic and printing technology utilized and the color values cited in the Detailed Botanical Description accurately describe the colors of the new *Canna*.

DETAILED BOTANICAL DESCRIPTION OF THE PLANT

The following is a detailed description of one-year-old plants of the new cultivar as grown in 2-gallon containers under 6 mm poly and natural lighting in Louisville, Ky. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms continuously during active growth in Louisville, Ky.

*Plant type*.—Deciduous, tropical, perennial often grown as an annual in cold climates.

*Plant habit*.—Upright, mid-sized, and compact.

*Height and spread*.—Average of 1.22 m in height and width in the landscape.

*Hardiness*.—At least in U.S.D.A. Zones 7b to 12.

*Diseases and pests*.—No susceptibility to diseases or pests has been observed.

*Roots*.—Fleshy from rhizomes.

*Propagation type*.—Rhizome division.

*Root development*.—Rooting initiates in 2 to 5 weeks, a young plant is produced from a rhizome in 2 to 5 weeks.

Stem description:

*Stem size*.—An average of 30 cm in length and an average of 3 cm in width (with sheaths).

*Stem type*.—Stout, rounded, surrounded by sheathed leaf petioles.

*Stem color*.—144A.

*Stem surface*.—Smooth and glossy.

Foliage description:

*Leaf shape*.—Broadly ovate.

*Leaf division*.—Simple.

*Leaf base*.—Cuneate.

*Leaf apex*.—Aristate to apiculate.

*Leaf venation*.—Pinnate, matching leaf colors, center vein more conspicuous and prominent, striated, with a center stripe that is a blend of N138A, 145A, 145B and 145C in color.

*Leaf margins*.—Entire, slightly wavy.

*Leaf attachment*.—Petiolate.

*Leaf arrangement*.—Alternate with petioles sheathed.

*Leaf surface*.—Glabrous on upper surface and lower surface, upper surface slightly glossy, lower surface matte.

*Leaf orientation*.—Emerge upright and become nearly horizontal and slightly upright when mature.

*Leaf color*.—Young upper surface; 146A and 144A, thinly striped variegation and margins N144B and 145C, young lower surface; 146A, margins N144B and 145C, mature upper surface; 147A, variegation 150D, 142D, 11D, mature lower surface 147A, margins N144B and 145C.

*Leaf size*.—Average of 24 cm in length and 15 cm in width when mature.

*Leaf quantity*.—An average of 6 per shoot.

*Petioles*.—About 14 cm in length, an average of 1 mm in width, glabrous, smooth and slightly shiny, inner and outer surface, sulcate and clasping to stem the entire length, color inner surface; matches leaf surface colors.

Inflorescence description:

*Inflorescence type*.—Terminal raceme that elongates as individual flowers open; flowers with showy staminodes that are arranged spirally along the rachis and open sequentially during the bloom season.

*Inflorescence size*.—Average of 10 cm in length and 8 cm in diameter (dependant on number of blooms open).

*Flower buds*.—Linear in shape, an average of 3.5 cm in length and 3 mm in width, color; matches sepal color when petals are unexposed, with petals slightly exposed NN155B.

*Flower fragrance*.—None detected.

*Lastingness of inflorescence*.—Inflorescence blooms continuously during the bloom period, individual flowers last about 2 days.

*Flower quantity*.—Continuously produced throughout the bloom season, one to three open at one time.

*Flower type*.—Comprised of less showy sepals and petals and showy staminodes.

*Flower size*.—Average of 9.5 cm in length, 6.5 cm in width.

*Rachis*.—Average of 15 cm in length and 6 mm in diameter, young inner and outer surface; 144A, mature inner and outer surface; striated, 144A, 10A, 10B and 144C in color, glabrous surface, shape is round and becoming flattened on one side near apex, an average of 4 bracts; an average of 8.5 cm in length and 3.5 cm in width, curled inward, glabrous on both surfaces, clasping base, apex acuminate with small mucronate tip, 144A in color.

*Sepals*.—3, lanceolate in shape, truncate base, acuminate apex, about 5.5 cm in length and 1 cm in width, both surfaces glabrous and shiny, both surfaces 144A changing to NN155A at the tip.

*Petals*.—3, lanceolate in shape, truncate base, acute apex, about 8 cm in length and 4 mm in width, color both surfaces young and mature; NN155B and 1A.

*Pedicels*.—Average of 2 cm in length and 4 mm in width, glabrous and shiny surface, 144A in color.

*Staminodes*.—Sterile; 4, an average of 9.9 cm in length and 4.6 cm in width, obovate to elliptic in shape, apex round to pointed, base cuneate to narrower base about 2 cm in length and 1 cm in width with truncate base, margins slightly crenate (irregular) and wavy, color of upper and lower surfaces NN155B in color, spotted with 171A at the base.

Reproductive organs:

*Gynoecium*.—1 pistil, style is an average of 8 cm in length and 1.3 cm in width, narrowly club shaped, truncate base, margins smooth, color upper and lower surface; NN155B, glossy on upper and lower surface, stigma surrounds apex, is about 5 mm in length and 11B in color, ovary is inferior, about 6 mm in length and 3 mm in width, and 11C in color.

*Androecium*.—Stamen; 1, average of 3 cm in length, filament; adnate to edge of staminode, NN155A, 3 cm in length, anthers; average of 1.5 cm in length, slightly curved, NN155B in color and basifixed, pollen is moderate in quantity and 11A in color.

*Fruit and seed*.—Fruit; globose, tri-rounded pod sections, 144A in color, spiky surface very densely covered with single narrow, oblong, transparent fruits closest to 145A in color, minute in size; about 0.5 mm in length, seed; an average of 6 seeds per section, round in shape, shiny and smooth surface, N199A in color.

It is claimed:

1. A new and distinct cultivar of *Canna* plant named 'White Tiger' as herein illustrated and described.

* * * * *